United States Patent
Logan, Jr. et al.

(10) Patent No.: US 7,781,736 B2
(45) Date of Patent: Aug. 24, 2010

(54) TERAHERTZ FREQUENCY DOMAIN SPECTROMETER WITH CONTROLLABLE PHASE SHIFT

(75) Inventors: Ronald T. Logan, Jr., Pasadena, CA (US); Joseph R. Demers, Alhambra, CA (US)

(73) Assignee: Emcore Corporation, Albuquerque, NM (US)

( * ) Notice: Subject to any disclaimer, the term of this patent is extended or adjusted under 35 U.S.C. 154(b) by 0 days.

(21) Appl. No.: 12/465,219

(22) Filed: May 13, 2009

(65) Prior Publication Data

US 2009/0283680 A1    Nov. 19, 2009

Related U.S. Application Data

(60) Provisional application No. 61/054,344, filed on May 19, 2008.

(51) Int. Cl.
*G01N 21/21*    (2006.01)
*G01N 21/25*    (2006.01)
*G01J 5/02*    (2006.01)

(52) U.S. Cl. .............................. 250/339.07; 250/338.1; 250/341.1; 356/460; 356/462

(58) Field of Classification Search ............. 250/339.07, 250/341.1; 356/460, 462
See application file for complete search history.

(56) References Cited

U.S. PATENT DOCUMENTS

| | | | |
|---|---|---|---|
| 4,594,511 | A | 6/1986 | Cooper et al. |
| 5,379,309 | A | 1/1995 | Logan, Jr. |
| 5,623,145 | A | 4/1997 | Nuss |
| 6,304,219 | B1 | 10/2001 | Rothe et al. |
| 6,348,683 | B1 * | 2/2002 | Verghese et al. ......... 250/214.1 |
| 6,545,785 | B1 | 4/2003 | Heflinger et al. |
| 6,811,552 | B2 | 11/2004 | Weil, Sr. et al. |
| 6,816,647 | B1 | 11/2004 | Rudd et al. |
| 6,844,552 | B2 | 1/2005 | Zhang et al. |

(Continued)

FOREIGN PATENT DOCUMENTS

EP    1233527 A1    8/2002

(Continued)

OTHER PUBLICATIONS

Bjanason, J.E., T.L.J. Chan, A.W.M. Lee and E.R. Brown (2004). "ErAs:GaAs Photomixer with two decade tenability and 12 μW Peak Output." Applied Physics Letters (85) 18: p. 3983-5.*

(Continued)

*Primary Examiner*—David P Porta
*Assistant Examiner*—Casey Bryant
(74) *Attorney, Agent, or Firm*—Coats & Bennett, P.L.L.C.

(57) ABSTRACT

An apparatus for analyzing, identifying or imaging an target including an integrated dual laser module coupled to a pair of photoconductive switches to produce cw signals in the range of frequencies from 100 GHz to over 2 THz focused on and transmitted through or reflected from the target; and a detector for acquiring spectral information from signals received from the target and using a multi-spectral homodyne process to generate an electrical signal representative of some characteristics of the target with resolution less than 250 MHz. The photoconductive switches are activated by laser beams from the dual laser module. The lasers in the module are tuned to different frequencies and a phase shifter in the path of one beam allows the beams to have an adjustable phase difference.

17 Claims, 6 Drawing Sheets

U.S. PATENT DOCUMENTS

| | | | |
|---|---|---|---|
| 6,849,852 B2 | 2/2005 | Williamson | |
| 6,865,014 B2 | 3/2005 | Ciesla et al. | |
| 7,126,078 B2 | 10/2006 | Demers et al. | |
| 7,174,037 B2 | 2/2007 | Arnone et al. | |
| 7,291,835 B2 * | 11/2007 | Overney | 250/288 |
| 7,291,839 B1 * | 11/2007 | Demers et al. | 250/341.1 |
| 7,439,511 B2 * | 10/2008 | Demers | 250/341.1 |
| 7,535,005 B2 * | 5/2009 | Demers | 250/341.1 |
| 2003/0155512 A1 | 8/2003 | Arnone et al. | |
| 2005/0162658 A1 * | 7/2005 | Pepper | 356/451 |
| 2006/0214107 A1 * | 9/2006 | Mueller | 250/341.8 |
| 2006/0255277 A1 | 11/2006 | Cole et al. | |
| 2008/0179528 A1 * | 7/2008 | Demers | 250/341.1 |
| 2008/0212974 A1 | 9/2008 | Davies et al. | |
| 2009/0015843 A1 * | 1/2009 | Demers et al. | 356/462 |
| 2009/0200472 A1 * | 8/2009 | Gregory | 250/339.07 |
| 2010/0080505 A1 | 4/2010 | Sartorius et al. | |

FOREIGN PATENT DOCUMENTS

| | | |
|---|---|---|
| GB | 2381121 A | 4/2003 |
| WO | WO 2007135382 A2 * | 11/2007 |

OTHER PUBLICATIONS

Arnone et al., "Applications of Terahertz (THz) Technology to Medical Imaging," *Proc. Spie Terahertz Spectroscopy Applicat. II*, 3823:209-219 (1999).

Arnone et al., "Terahertz Imaging Comes into View," *Phys. World*, 35-40 (2000).

Bartels et al., "Femtosecond Time-Resolved Optical Pump-Probe Spectroscopy at Kilo Rates Over Nanosecond-Time-Delays Without Mechanical Delay Line," *Appl. Phys. Lett.*, 88:04117 (2006).

Bartels et al., "High-Resolution THz Spectrometer with kHz Scan Rates," *Optics Express*, 14(1):430-437 (2006).

Chang et al., "Power Scalable Compact THz System Based on an Ultrafast Yb-doped Fiber Amplifier," *Optics Express*, 14(17):7909-7913 (2006).

Chen et al., "Spectroscopic Applications and Frequency Locking of THz Photomixing with Distributed-Bragg-Reflector Diode Lasers in Low-Temperature-Grown GaAs," *Appl. Phys. Lett.*, 71(12):1601-1603 (1997).

Gutierrez, "An Electro-Optical Frequency Shifter," NASA's Jet Propulsion Laboratory, (2000), Available at <URL: http://www.nasatech.com/Briefs/Sept00/NPO20531.html>.

Hu et al., "Imaging with Terahertz Waves," *Optics Letters*, 20(16)1716-1718 (1995).

Hunsche et al., "Terahertz 'T-Ray' Tomography," *Proc. SPIE Int. Millimeter Submillimeter Waves Applicat. IV.*, 50(3):426-433 (1998).

Janke et al., "Asynchronous Optical Sampling for High-Speed Characterization of Integrated Resonant Terahertz Sensors," *Optics Letters*, 30(11)1405-1407 (2005).

Jiang et al., "Terahertz Imaging via Electrooptic Effect," *IEEE Trans. Microwave Theory Tech.*, 47:2644-2650 (1999).

McGrath et al., "Superconductive Hot Electron Mixers with Ultra Wide RF Bandwidth for Heterodyne Receiver Applications Up to 3 THz," *Proceedings of the ESA Symposium*, 401-404 (1997).

McIntosh et al., "Terahertz Measurements of Resonant Planar Antennas Coupled to Low-Temperature-Grown GaAs Photomixers," *Appl. Phys. Lett .*, 69(24):3632-3634 (1996).

Mittleman et al., "T-Ray Imaging," *IEEE J. Select. Topics Quantum Electron*, 2:679-692 (1996).

Saleh et al., "Fundamentals of Photonics," Wiley-Interscience, pp. 719-720, 823-825 (1991).

Siegel, "Terahertz Technology," *IEEE Transactions on Microwave Theory and Techniques*, 50(3):915-917 (2002).

Verghese et al., "Generation and Detection of Coherent Terahertz Waves using Two Photomixers," *Applied Physics Letters*, 73(26):3824-3826 (1998).

Wu et al., "Two-Dimensional Electro-Optic Imaging of THz Beams," *Appl. Phys. Lett.*, 69(8):1026-1028 (1996).

Yasui et al., "Terahertz Frequency Comb by Multifrequency-Heterodyning Photoconductive Detection for High-Accuracy, High Resolution Terahertz Spectroscopy," *Applied Physics Letters*, 88(241104):1-3 (2006).

U.S. Appl. No. 12/062,772 of Ronald T. Logan, Jr. et al., filed Apr. 4, 2008, entitled "Terahertz Frequency Domain Spectrometer with Integrated Dual Laser Module" (unpublished).

English translation of abstract of EP1233527. 1 page. European Patent Office. http://ep.espacenet.com/?locale=en_EP.

* cited by examiner

TERAHERTZ FREQUENCY DOMAIN SPECTROMETER WITH CONTROLLABLE PHASE SHIFT

REFERENCE TO RELATED APPLICATIONS

This application is related to U.S. patent application Ser. No. 11/796,069, filed Apr. 5, 2007 which is a continuation-in-part of U.S. patent application Ser. No. 11/669,685 filed Jan. 31, 2007. This application claims priority to U.S. Provisional Application No. 61/054,344 filed May 19, 2008.

BACKGROUND OF THE INVENTION

1. Field of the Invention

The invention relates to microwave, millimeter wave and submillimeter wave spectroscopy systems and components and in particular to a method and apparatus for controlling the phase shift of the optical signal in a homodyne or heterodyne transceiver useful for terahertz spectroscopy.

2. Description of the Related Art

Terahertz devices and systems generally employ electromagnetic energy between 300 GHz and 3 terahertz (3 THz), or wavelengths from 100 to 1000 microns (0.1 to 1.0 millimeters), which is also referred to as the submillimeter or far-infrared region of the electromagnetic spectrum. Terahertz energy can be created, for example, using short-pulsed lasers, heterodyne lasers, electronic diode multipliers, free-electron lasers, and BWOs.

One important application of terahertz systems is THz spectroscopy. Terahertz spectroscopy presents many new instrumentation and measurement applications since certain compounds and objects can be identified and characterized by a frequency-dependent absorption, dispersion, and/or reflection of terahertz signals which pass through or are reflected from the compound or object. One implementation of such spectroscopy is time domain spectroscopy, in which a sequence of femtosecond pulses from a mode locked laser are focused onto suitable semiconductor material to produce THz radiation. The radiation is focused or directed to a target or sample to be analyzed, and a detector or detector array is used to collect any signals propagated through or reflected from the object. Since such measurements are made in the time domain by collecting the timed sequence of pulses, the signals must then be processed by a Fourier transformation to recover the desired frequency domain spectral information.

By scanning every point or "pixel" on that object, either on a focal plane or in successive focal planes at different ranges, it is also possible for such a time domain system to perform imaging of the surface or interior cross-sections or layers of the object. This non-invasive imaging technique is capable of differentiating between different materials, chemical compositions, or molecules in the interior of an object. However, the process of performing a Fourier transform from the time domain into the frequency domain imposes limitations on the frequency resolution and upon the ability to look at specific frequency windows.

As noted in a review article by Peter H. Siegel in IEEE Transactions on Microwave Theory and Techniques, Vol. 50, No. 3, 915-917 (March 2002), terahertz time-domain spectroscopy was described by Nuss and others at Bell Laboratories in the mid-1990s (B. B. Hu and M. C. Nuss, "Imaging with terahertz waves," Opt. Lett., vol. 20, no. 16, pp. 1716-1718, Aug. 15, 1995; D. M. Mittleman, R. H. Jacobsen, and M. C. Nuss, "T-ray imaging," IEEE J. Select. Topics Quantum Electron., vol. 2, pp. 679-692, September 1996), and recently commercialized by at least two companies, Picometrix, LLC of Ann Arbor, Mich. (D. D. Arnone et al., "Applications of terahertz (THz) technology to medical imaging," in Proc. SPIE Terahertz Spectroscopy Applicat. II, vol. 3823, Munich, Germany, 1999, pp. 209-219) and Teraview Ltd. (a spinoff of Toshiba Research Europe) located in Cambridge, England (D. Arnone, C. Ciesla, and M. Pepper, "Terahertz imaging comes into view," Phys. World, pp. 35-40, April 2000).

In situ measurements of the transmitted or reflected terahertz energy incident upon a small sample are processed to reveal spectral content (broad signatures only), time of flight data (refractive index determination, amplitude and phase, and sample thickness), and direct signal strength imaging. The principle involves generating and then detecting terahertz electromagnetic transients that are produced in a photoconductive switch (PCS) or an optical crystal by intense femtosecond optical laser pulses. The laser pulses are beam split and synchronized through a scanning optical delay line and made to strike the terahertz generator and detector in known phase coherence. By scanning the delay line and simultaneously gating or sampling the terahertz signals incident on the detector, a time-dependent waveform proportional to the terahertz field amplitude is produced. Fourier transformation of this waveform yields information about the frequency spectral content. Transverse scanning of either the terahertz generator or the sample itself allows a 2-D image to be built up over time.

Other developments in terahertz spectroscopy include rapid scanning (S. Hunsche and M. C. Nuss, "Terahertz 'T-ray' tomography," in Proc. SPIE Int. Millimeter Submillimeter Waves Applicat. IV Conf, San Diego, Calif., July 1998, pp. 426-433.) and true 2-D sampling using charge-coupled device (CCD) arrays (Z. Jiang and X.-C. Zhang, "Terahertz imaging via electrooptic effect," IEEE Trans. Microwave Theory Tech., vol. 47, pp. 2644-2650, December 1999.). In the Picometrix and Lucent Technologies systems, the generator and detector are based on the photoconductive effect in low-temperature-grown (LTG) gallium-arsenide (GaAs) compound semiconductor material, or radiation-damaged silicon on sapphire semiconductor. The Teraview system uses terahertz generation by difference-frequency mixing in a non-linear crystal (ZnTe) and detection via the electrooptical Pockels effect (measuring the change in birefringence of ZnTe induced by terahertz fields in the presence of an optical pulse) as first demonstrated by Zhang at the Rensselaer Polytechnic Institute (RPI), Troy, N.Y. (see Q. Wu, T. D. Hewitt, and X.-C. Zhang, "Two-dimensional electro-optic imaging of THz beams," Appl. Phys. Lett., vol. 69, no. 8, pp. 1026-1028, Aug. 19, 1996.). The femtosecond optical pulses are currently derived from relatively expensive Ti:Sapphire lasers, but other proposals include longer wavelength, especially 1.5 micron, solid-state systems that can take better advantage of fiber technology (see D. M. Mittleman, R. H. Jacobsen, and M. C. Nuss, "T-ray imaging," IEEE J. Select. Topics Quantum Electron., vol. 2, pp. 679-692, September 1996). The RF signals produced by the optical pulses typically peak in the 0.5-2 THz range and have average power levels in the microwatt range and peak energies around a femtojoule. This makes T-ray imaging an attractive tool for medical applications (noninvasive sampling), as well as for nondestructive analysis of biological materials or electronic parts. One drawback of prior art designs is the need to scan the delay line slowly and over a distance of the desired wavelength resolution (e.g., a 1 GHz resolution would require a 7.5 cm scan of the movable optical delay line) and the inability to interrogate discrete frequencies of interest. The high degree of positional tolerance required to be maintained on the movable optical delay assembly limits the utility of this approach in applications where compact size and operation in uncontrolled environments are required with wide temperature excursions and/or shock and vibration. Also, in many cases, higher frequency resolution and accuracy are desired than is easily possible with scanning delay-line systems, such as in analysis of Doppler-limited molecular rotational transitions in low-pressure gases.

The need for a multi-octave tunable spectrometer in the THz region is justified by the new suite of applications relating to materials identification facing researchers and system developers today. Historically, the THz field has been dominated by radio astronomers and chemists usually concerned with detecting trace amounts of small gaseous molecules in the interstellar medium or in the Earth's upper atmosphere. The low pressure of the media involved would often lead to narrow, Doppler-limited absorption lines, sometimes less than 1 MHz in linewidth. In roughly the last decade, the THz application landscape has changed dramatically with the discovery and demand for detection and imaging of larger molecules, particularly biomolecules and bioparticles. This includes, for example, proteins and vitamins using frequency sweeps typically above 1 THz, and bacterial spores and nucleic acids using frequency sweeps typically below 1 THz. In most cases the biomolecular and bioparticle absorption occurs not in the form of narrow lines, but rather as broad "signatures", typically 1 to 10 GHz or wider. Solid materials such as explosive agents and their precursors are also of particular interest for terahertz detection applications. Nanostructured materials are also of interest for high-resolution THz studies, due to the similarity in size of the nanostructures and the wavelength of THz radiation. Solid disordered materials typically have similarly broad absorption features due to phonons. Crystalline materials of interest may also exhibit sharper resonances. In many cases, there may only be a few limited frequency bands of interest that show strong THz absorption in a particular material of interest. A multi-octave spectrometer capable of measuring small discrete windows of frequencies with high resolution would allow faster measurement of signatures in the same session, increasing confidence and specificity.

In addition to the time-domain spectrometers noted above, frequency domain systems are also known (See the paper by Verghese et al., "Generation and detection of coherent terahertz waves using two photomixers," Appl. Phys. Lett., vol. 73, no. 26, pp. 3824-3826, Dec. 28, 1998.). One prior art terahertz spectrometer system is described in U.S. Pat. No. 7,291,835, assigned to the common assignee, and hereby incorporated by reference. The system includes a laser illumination arrangement that generates a pair of source laser beams incident on a source photomixer device or PCS to cause emission of subcentimeter radiation, at least a portion of which interacts with the remote sample to generate a "sample influenced radiation" which is then incident on a detector photomixer device. A second pair of laser beams is incident on the detector to produce an optical component of the detector photocurrent that is offset in frequency with respect to the detected source laser energy. As a result, the detector generates a frequency down-converted electrical output signal responsive to and characteristic of the sample-influenced radiation.

The concept of photomixing is known from—for example—U.S. Pat. 6,348,683 which describes a method of generating quasi-optical signals using an optical-heterodyne converter or photometer source. Photomixer sources are compact solid-state sources that use two single frequency tunable lasers, such as diode lasers, to generate a terahertz difference frequency by photoconductive mixing in a photoconductive material. Photomixer sources using low-temperature-grown (LTG) GaAs have been used to generate coherent radiation at frequencies up to 5 THz. In particular the patent describes a transceiver for transmitting and receiving terahertz radiation. The transceiver includes a first laser that generates radiation at a first frequency and a second laser that generates radiation at a second frequency. The difference frequency, equal to the difference between the first and the second laser frequencies, is tunable by the user from microwave through terahertz frequencies by adjusting the frequency of one or both lasers. A transmitter includes a first photomixer that is optically coupled to the first and the second light source. A first radiative element or antenna is electrically coupled to the first photomixer. In operation, the first antenna radiates a terahertz signal generated by the first photomixer at the difference frequency. A receiver includes a second antenna to receive the signal from the target radiated by the first antenna. The second antenna generates a time varying voltage proportional to the terahertz return signal. A second photomixer is electrically coupled to the second antenna and is optically coupled to the first and the second light source. The second photomixer generates a current signal in response to the time varying voltage generated by the second antenna.

Commercial terahertz frequency-domain spectrometers, such as the Emcore PB7100 manufactured by Emcore Corporation in Alhambra, California, rely on coherent detection of the transmitted THz signal using a photomixer that is excited optically by a sample of the same heterodyne signal that produces the source THz signal. These frequency domain systems typically exhibit a characteristic repeating interference pattern in their raw data sets (i.e., the spectrogram collected by the instrument has a periodic pattern of peaks and nulls when plotted against frequency). This interference pattern is expected, as it is an inherent feature of any coherent unbalanced interferometer in which the input frequency is swept over a large range of frequencies. The peaks and nulls occur at frequency separation equal to the product of c/n L, where c is the speed of light, n is the index of refraction, and L is the path length imbalance between the interferometer arms. The interference could be avoided in principle if the path lengths of both the optical and THz paths were precisely balanced at all optical and THz frequencies. However, this is neither practical nor possible in many cases. Indeed, the propagation of the THz energy through air at sea level may introduce frequency dispersion due to the index of refraction of air, i.e., the index n becomes a function of frequency, so that n =n(f). Such a frequency-dependent index could cause the interference effect, even if the paths were perfectly balanced. Moreover, this frequency dependence could change with atmospheric conditions, such as dust and humidity. In the case of a sample being interrogated by the THz beam, the interferogram contains the detailed information of the complex index of refraction and absorption of the sample.

In the Emcore PB7100, this interference pattern may be "smoothed" by performing a running average of the data set, yielding a lower-resolution absorption spectrum for the sample being interrogated that provides useful information for absorption features with multi-GHz widths. Although such a technique mitigates the interference, the processing limits the frequency resolution of the data collected by the spectrometer, as well as throws away valuable information related to the phase of the signal at each frequency. Attempts to remove the interference and preserve frequency resolution, through mathematical processing of the data, have been unsuccessful to date for reasons that are not well-understood.

It may be due to frequency dispersion of the THz signal in air, or due to frequency dispersion of the antenna elements, or a combination of the two.

SUMMARY OF THE INVENTION

1. Objects of the Invention

It is an object of the present invention to provide an improved frequency domain terahertz spectrometer using two continuously tunable semiconductor lasers with the phase of at least one of the lasers being controllable.

It is another object of the present invention to provide a terahertz spectrometer for the identification of a target spectrum with high resolution and detection sensitivity.

It is also another object of the present invention to mitigate the interference effect in a frequency-domain terahertz spectrometer with controllable phase.

It is an object of the present invention to provide a method for adjusting the phase difference between two source lasers forming a composite optical beam used in a frequency-domain terahertz spectrometer.

It is another object of the present invention to provide a method for adjusting the phase of a laser in a terahertz spectrometer to provide higher frequency specificity and resolution.

It is also another object of the present invention to provide a terahertz spectrometer with adjustable resolution at specific frequency regions of interest.

It is still another object of the present invention to provide a field portable terahertz spectrometer system in a highly compact configuration capable of identifying or imaging an object utilizing a laser with adjustable or controllable phase.

Some implementations may achieve fewer than all of the foregoing objects.

2. Features of the Invention

Briefly, and in general terms, an apparatus according to an aspect of the present invention comprises first and second lasers having tunable frequencies for producing a first composite output beam; a source of CW signals in the range of frequencies from 100 GHz to over 2 THz including a first photoconductive switch activated by the composite optical beam; a radiative element causing the signals to be substantially simultaneously focused on or through said target; and a detector for acquiring spectral information reflected from the target and coupled to a second composite optical beam having an adjustable phase difference from the first composite beam for generating an electrical signal representative of some characteristic of the target.

In another aspect, the invention provides a method for terahertz spectroscopy including providing a source of CW signals in the range of frequencies from 100 GHz to over 2 THz, including a first photoconductive switch activated by a first composite optical laser beam; causing the signals to be substantially simultaneously focused on or through said target; and acquiring spectral information from the target and coupled to a second composite optical beam having an adjustable phase difference from the first composite beam for generating an electrical signal representative of some characteristic of the target.

In another aspect, the invention provides an apparatus for analyzing, identifying or imaging a target using an integrated laser module including first and second lasers; a source of constant wave (CW) radiation in the range of frequencies from 100 GHz to over 2 THz including a first PCS activated by an optical beam resulting in a CW frequency that is the difference frequency of said first and second lasers; a radiative element for causing said signals to be substantially simultaneously focused onto or through said target; and a detector for acquiring spectral information transmitted through the target or reflected from the target coupled to a second composite optical beam having an adjustable phase difference from the first composite beam.

Additional objects, advantages, and novel features of the present invention will become apparent to those skilled in the art from this disclosure, including the following detailed description as well as by practice of the invention. While the invention is described below with reference to preferred embodiments, it should be understood that the invention is not limited thereto. Those of ordinary skill in the art having access to the teachings herein will recognize additional applications modifications and embodiments in other fields, which are within the scope of the invention as disclosed and claimed herein and with respect to which the invention could be of utility.

BRIEF DESCRIPTION OF THE DRAWINGS

These and other features and advantages of this invention will be better understood and more fully appreciated by reference to the following detailed description when considered in conjunction with the accompanying drawings wherein.

Figure 1:
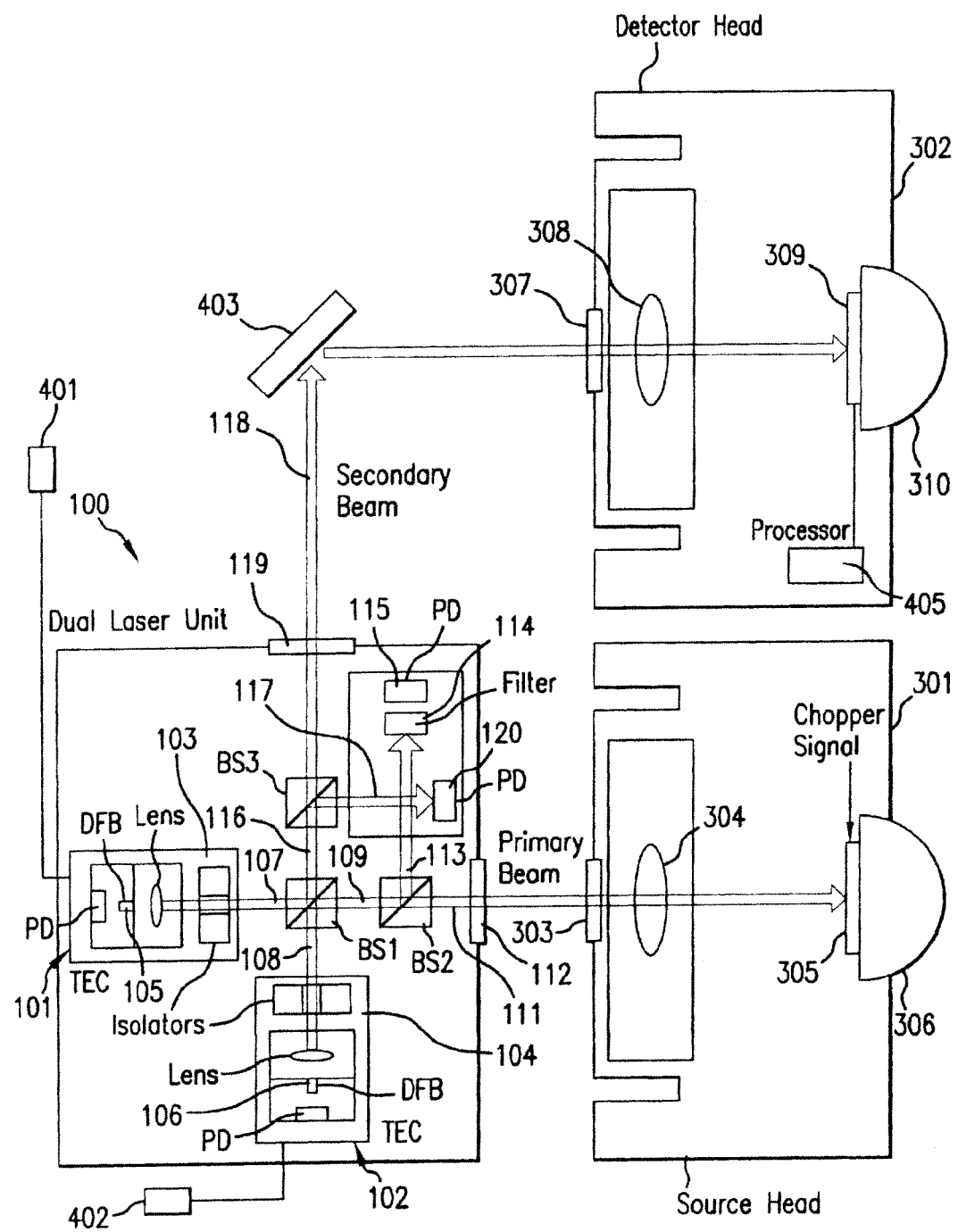
FIG. 1 is a block diagram of a dual laser module used in the Emcore PB7100, a frequency-domain THz spectrometer of the prior art.

The novel features and characteristics of the invention are set forth in the appended claims. The invention itself, however, as well as other features and advantages thereof, will be best understood by reference to a detailed description of a specific embodiment, when read in conjunction with the accompanying drawings.

DETAILED DESCRIPTION OF THE PREFERRED EMBODIMENT

Details of the present invention will now be described, including exemplary aspects and embodiments thereof. Referring to the drawings and the following description, like reference numbers are used to identify like or functionally similar elements, and are intended to illustrate major features of exemplary embodiments in a highly simplified diagrammatic manner. Moreover, the drawings are not intended to depict every feature of actual embodiments or the relative dimensions of the depicted elements, and are not drawn to scale.

As noted above, in the frequency-domain technique for terahertz spectroscopy, CW THz radiation is produced through photomixing of the combined output of two single-frequency diode lasers in a low temperature grown GaAs photomixer or PCS. The wavelength of one (or both) of the lasers is tuned to vary the THz output frequency. In most spectroscopic applications of photomixing to date, the THz output beam from the PCS has been coupled to a sensitive broadband thermal detector (e.g., a liquid He bolometer or Golay cell), making the overall signal processing incoherent and phase insensitive.

In a different embodiment, coherent (homodyne) detection in a terahertz spectrometer can be achieved at room temperature by mixing the same optical radiation from the diode lasers in a detector PCS onto which the THz signal is also incident. This provides similar or greater sensitivity and faster data acquisition then the incoherent technique, and preserves phase information.

Some of the benefits of the coherent frequency-domain technique compared to the time-domain spectroscopy (TDS) technique are: (1) no moving parts (i.e. no mechanical scanning delay line), (2) higher frequency resolution, and (3) the ability to selectively scan specific frequency regions of interest with adjustable resolution. Also, unlike TDS systems, CW photomixing results in substantially all of the THz power being concentrated at a single THz frequency, thus improving spectral density and signal-to-noise ratio at that frequency. However, previously it has been difficult to realize practical frequency-domain spectrometers due to the challenges associated with the construction and control of the dual lasers, namely mode-matching and co-collimation of the two laser beams and precise control of their difference frequency.

One frequency-domain spectrometer of the present invention is depicted in the block diagrams of FIGS. 1 and 2. In a preferred embodiment, the spectrometer utilizes a highly-integrated dual semiconductor laser module 100 the details of which are more particularly described in U.S. patent application Ser. No. 12/062,772 and shown in FIG. 1. The dual laser module of FIG. 1 will be described in detail below in order to provide a example of the type of system that may employ the present invention, although the present invention may be implemented in other types of spectrometers. For clarity, we have depicted the invention herein as employing free-space optical coupling between the lasers and other components. However, for example, the lasers could instead be individually packaged in modules with fiber-optic outputs, and connected via optical fibers to fiber-optic couplers, phase-shifters, etc., to realize the same topology and functionality of the present invention.

Figure 2A:
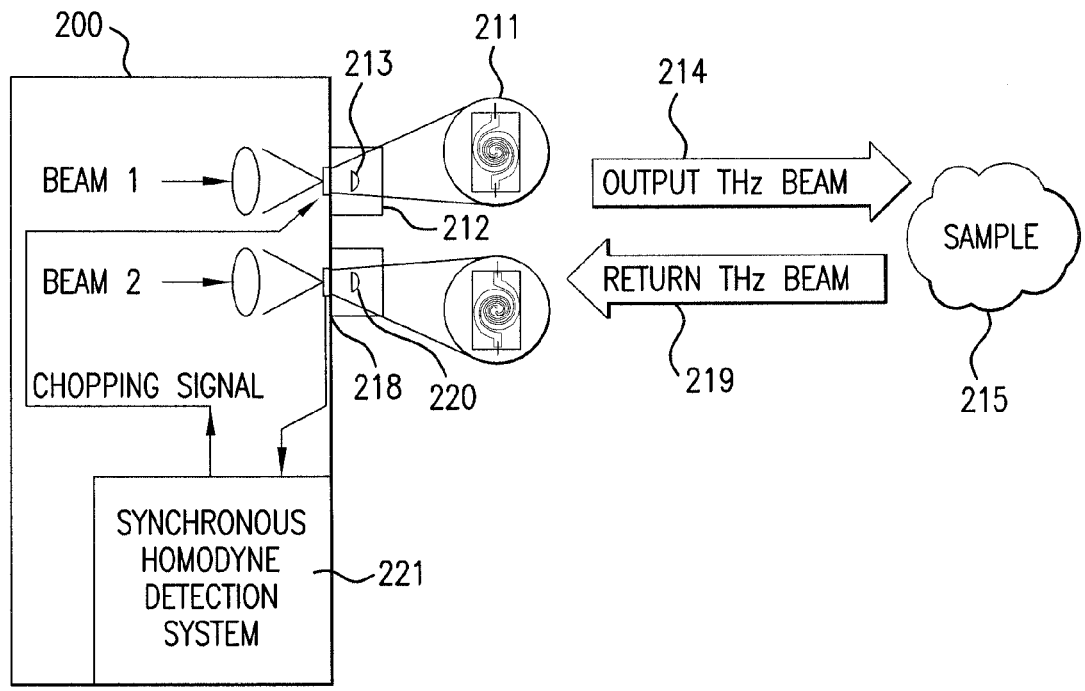
FIG. 2A is a block diagram of a frequency domain terahertz spectrometer according to the present invention which employs reflection from the sample.
Figure 2B:
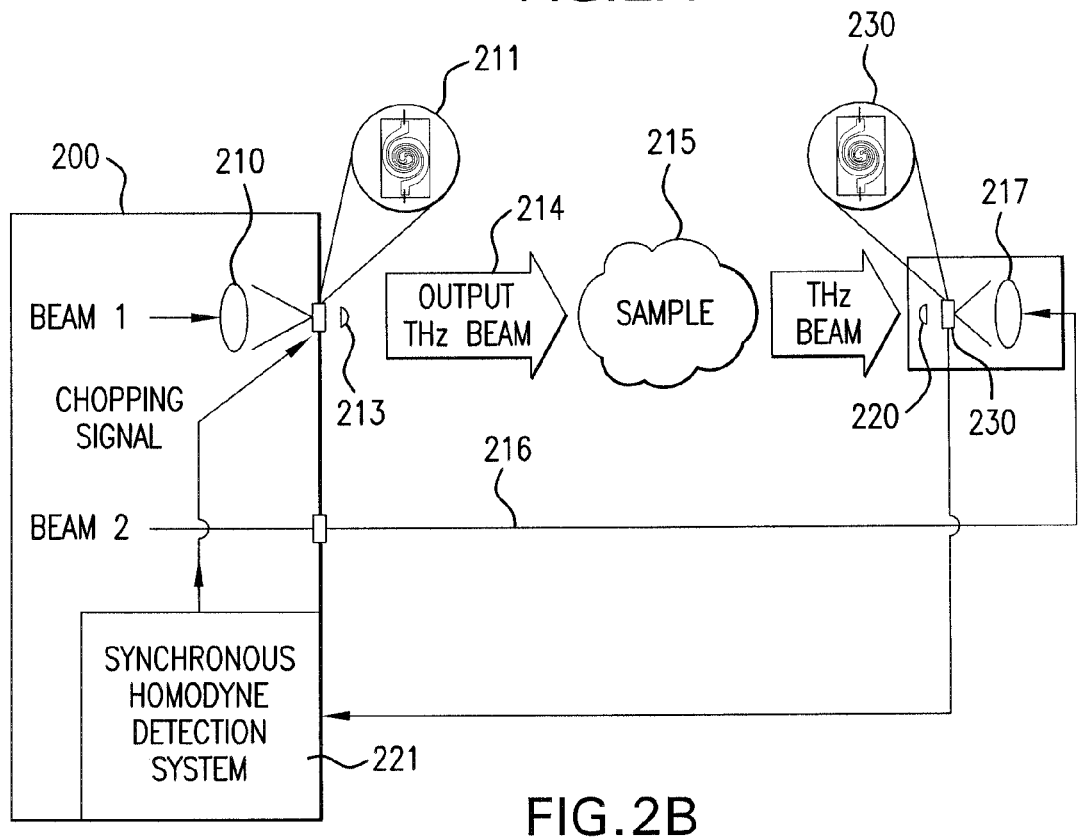
FIG. 2B is a block diagram of a frequency domain terahertz spectrometer according to the present invention which employs transmission from the sample.

In a terahertz spectrometer, the terahertz radiation is focused or directed to the target sample to be analyzed, and a detector or detector array is arranged to collect the signal propagated through or reflected from that target. The two modes of transmission or reflection from the target are illustrated in FIG. 2A and 2B. The configuration or arrangement of FIG. 2A depicts reflection, and FIG. 2B depicts transmission through the target sample by appropriate placement of the source head 301 (see, FIG. 1) and the detector head 302. The spectrometer may further incorporate a processor and other electronics for determining the identity or composition of the target, and/or printing or displaying the results so that the information is readily available to the user.

Turning to FIG. 2A, the output of a heterodyne laser source, labeled BEAM 1, applied to a lens 210 which focuses the beam to a spot of approximately ten microns in diameter on the surface of a low temperature grown gallium arsenide photoconductive switch 211. The heterodyne laser beam focus is situated at a gap in an antenna circuit patterned on the surface of the PCS, shown as a spiral in FIG. 2A. A slowly time-varying ("chopped") electrical bias signal is applied to the antenna on the PCS. The THz variation in the intensity of the heterodyne laser signal produces a THz modulation of the conductance in the PCS material, which in turn produces a THz current in the antenna patterned on the surface of the PCS. This current is further modulated by the "chopping" signal. This current in the antenna produces terahertz radiation in the THz frequency range from typically 100 GHz to over 2 THz, depending on the difference frequency of the heterodyne laser source.

The terahertz radiation so produced is emitted from PCS device 211 and then collimated and collected by a silicon lens 213, preferably a hemispherically shaped structure approximately two to three centimeters in diameter. Additional lenses (not shown), composed of TEFLON or other suitable materials may be placed downstream of the lens 213 to collimate the RF beams into an output THz beam 214. Beam-shaping mirrors may also be used in lieu of or in addition to the silicon lens 213.

The outgoing terahertz radiation beam is relatively low power, about 1 to 10 microwatts. The target sample 215 will absorb and transmit some radiation, and also reflect a portion of the radiation back in the direction of the source or user, as shown by the return THz beam 219. It is estimated that the return power at the receiver antenna should be at least 1 to 10 nanowatts in order for useful signal data to be able to be processed.

On the receiver side, the return signal 219 is directed to a second silicon lens 220 which focuses the return THz beam to the antenna on the surface of a second LTG GaAs PCS 218 which is similar to 211 and which acts as a THz detector. The second output of the heterodyne laser, labeled BEAM 2, is also directed to the PCS 218 and the two signals are combined in the LTG GaAs PCS detector 218. This arrangement yields homodyne downconversion of the received THz signal to a baseband frequency equal to the "chopping" frequency, that may then be detected by a synchronous circuit with adjustable bandwidth to filter unwanted noise, such as a "lock-in" amplifier, or similar arrangement, 221.

FIG. 2B is a block diagram of a representative spectrometer 200 arranged to employ transmission through the sample 215. The output of a heterodyne laser, labeled BEAM 1, is applied to a lens 210 which focuses the beam to a spot of approximately ten microns in diameter on the surface of a low temperature grown gallium arsenide photoconductive switch 211. The heterodyne laser beam focus is situated at a gap in an antenna circuit patterned on the surface of the PCS, shown as a spiral 211 in FIG. 2B. A slowly time-varying ("chopped") electrical bias signal is applied to the antenna on the PCS. The THz variation in the intensity of the heterodyne laser signal produces a THz modulation of the conductance in the PCS material, which in turn produces a THz current in the antenna patterned on the surface of the PCS. This current is further modulated by the "chopping" signal. This current in the antenna produces terahertz radiation in the THz frequency range from typically 100 GHz to over 2 THz, depending on the difference frequency of the heterodyne laser source. The terahertz radiation emitted from the PCS device 211 is collimated and collected by a silicon lens 213, preferably a hemispherically shaped structure approximately two to three centimeters in diameter. Additional lenses (not shown), composed of TEFLON or other suitable materials may be placed downstream of the lens 213 to collimate the RF beams into the output THz beam 214. The target or sample 215 to be identified will absorb and transmit some radiation to the detector head 302 placed on the opposite side of the sample 215. The transmitted THz signal is directed to a lens 220 which focuses the beam to the antenna on the surface of a second LTG GaAs PCS 230 which is similar to 211 and which acts as the detector. A second output of the heterodyne laser, labeled BEAM 2, is also directed to a lens 217 which focuses the beam to a ten micron spot on the surface of a LTG GaAs PCS 230, and the two signals are combined in the LTG GaAs PCS detector 230 to yield homodyne downconversion of the transmitted THz signal, which is then applied to a synchronous detection system 221.

Returning back to FIG. 1, there is depicted a housing 100 incorporating the optical and electro-optical components suited for incorporation as a subassembly in the spectrometers of FIG. 2A and 2B. Lasers 105 and 106 are preferably two 783 nm distributed feedback (DFB) or distributed Bragg reflector (DBR) laser diodes with single-longitudinal-mode and single spatial-mode operation over the desired range of wavelengths, available from various vendors (for example, Eagleyard Photonics GmbH of Berlin, Germany.) In the present invention it would also be possible to utilize one or more external-cavity tunable semiconductor lasers such as are available from Emcore Corporation. Also, it is noted that two or more DFB or DBR lasers could be fabricated on a common semiconductor substrate with a semiconductor waveguide combiner element to produce a single optical output containing both laser frequencies. In this particular embodiment, the output of one laser is adjusted to 783 nm, and the output of the other laser is at 784 nm. The diode laser packaging permits co-collimation of the laser beams to a very high degree of precision, and the design allows very precise frequency control of the lasers and monitoring the laser output through digital signal processing to achieve more accurate control over the laser output beam frequencies and achieve a resolution of less than 250 MHz in a terahertz spectrometer.

In one embodiment, the laser diode chips 105 and 106 are mounted on independent Peltier thermoelectric coolers (TECs) 103 and 104. The center wavelengths of the lasers are nominally 783 nm at 25° C., but the wavelengths may be temperature-tuned with a tuning coefficient of approximately 0.1 nm per ° C. Therefore, a 50 degree C. temperature range of operation from −10 degrees C. to +40 degrees C. will yield a frequency range of approximately 5 nm. For the purposes of illustration only, if the DFB lasers are selected such that their center wavelengths at 25 C are at 782 nm and 784 nm, respectively, then a thermal tuning range of −10 C to +40 C on each laser chip will permit generation of offset wavelengths 0 nm to approximately 7 nm, corresponding to a range of offset frequencies from 0 Hz to 3.4 THz. The thermal mass on the controlled surface of the TECs is such that it allows rapid frequency tuning. In the case of DBR laser diode chips, the Bragg-reflection section of each laser is adjusted electronically to vary the laser frequency. Wider offset frequency ranges may also be possible by employing wider temperature excursion, or by using DBR lasers. The output from each laser is collimated with an aspheric lens mounted on a precision lens-mount with sub-micron adjustment capability (see, e.g. U.S. Pat. No. 7,126,078). The laser outputs are directed through optical isolators to prevent feedback into the lasers. A 50/50 beamsplitter BS1 is disposed in the path of the output beams 107 and 108 and is used to split the two beams into composite primary and secondary beams 109 and 116, which in a preferred embodiment are at right angles to each other. The lenses and the beamsplitter BS1 are advantageously adjusted so that beam overlap is sufficient to generate photomixing products.

In the present invention, the output beam 109 is directed along a first path to a second beamsplitter BS2, and the second beam 116 is directed along another path to a third beamsplitter BS3. The optical propagation path downstream of the lasers and throughout the unit 100 may be either free space or an appropriate single-mode polarization-maintaining optical fiber (PMF). In the case of optical fiber construction, the beamsplitters may be replaced with suitable optical waveguide couplers. As can be appreciated, the basic topology depicted in FIG. 1 uses free-space optical implementation which readily illustrates the various optical paths.

As shown in FIG. 1, the second beam splitter BS2 also produces primary 111 and secondary 113 beams which are shown as substantially at right angles to one another. The secondary beam 113 is applied to a filter 114, and then to a first photodiode 115. The output of the photodiode 115 is used to sample and measure the power of the composite beam 109, as will be subsequently described. The primary beam 111 is directed to a window 112 in the module 100 for output.

Similarly, the third beam splitter BS3 produces a primary 117 and a secondary beam 118 at substantially right angles to one another. The primary beam 117 is applied to a second photodiode 120. The output of the photodiode 120 is used to sample and measure the power of the composite beam 116, as will be subsequently described. The secondary beam 118 is directed to a window 119 in the module 100 for output.

FIG. 1 also depicts a first current source 401 which is coupled to laser 105 to drive it and modulate it with a low frequency 416 kHz tone, and a second current source 402 which is coupled to laser 106 to drive it and modulate it with a second low frequency 430 kHz tone. The use of such tones in connection with the composite optical signal will be subsequently discussed. Other tone frequencies may be selected as convenient.

A reflector element 403 in the path of secondary beam 118 is also depicted, as well as the source head 301 and the detector head 302.

The output beam 111 directed by the effect of the second beamsplitter BS2 exits the housing 100 through the window 112. This "primary beam" 111 is directed through a window 303 in the appropriately positioned source head 301, and then to a lens 304 in the source head 301 which focuses the beam to a spot of approximately ten microns in diameter on the surface of a PCS 305. The optical beam is focused into a gap in an antenna circuit patterned on the surface of the PCS device. An alternating electrical bias (i.e., "chopped") is applied to the antenna. The optical frequency signal directed to the surface of the PCS semiconductor device results in a modulation of the conductance of the gap in the antenna, which produces the emission of terahertz radiation from the PCS 305 in the frequency range 100 GHz to over 2 THz, corresponding to the offset frequency between the lasers 105 and 106.

The terahertz radiation emitted from the PCS device 305 is collimated and collected by a silicon lens 306 which is shown mounted to the source head 301. The lens 306 is preferably a hemispherically shaped structure approximately one centimeter in diameter. Additional lenses (not shown), composed of Teflon or other suitable materials may be placed downstream of the lens 306 to collimate the RF beams into the output THz beam (not specifically shown in this FIG). Beam-shaping mirrors may also be used in lieu of or in addition to the silicon lens.

As can be readily appreciated, the target sample (or other object/material to be identified) may absorb and transmit some radiation, and may also reflect a portion of the radiation back in the direction of the source.

As noted above, the second beam 116 is directed to a third beamsplitter BS3 where it is split two beams 117 and 118. The secondary beam 118 from beamsplitter BS3 exits the module 100 through a window 119, and is subsequently directed to the detector head 302. The secondary beam 118 is directed through window 307 in the detector head 302, and then to a lens 308 which focuses the beam to a spot of approximately ten microns in diameter on the surface of a PCS 309. The silicon lens 310 collects the radiation transmitted or reflected from the target, which is then detected by PCS 309 in the same manner as the systems depicted in FIGS. 2A and 2B. A signal resulting from this detection may be processed by processor 405, shown coupled to the PCS 309. The processor will typically be a synchronous detection circuit, such as a "lock-in" amplifier, that makes use of the electrical chopping signal applied to the source PCS as a reference for the synchronous detection process.

Advantageously and according to an aspect of the present invention, a terahertz frequency domain spectrometer system may be implemented using two ErAs:GaAs PCSs in a highly compact configuration, utilizing all solid-state components and no moving parts. The system utilizes a single package integration of two 783 nm DFB laser diodes with a high-resolution wavelength discriminator. Digital signal processing electronics provide precise frequency control and yields approximately 200 MHz accuracy of the THz signal frequency. Continuous frequency sweeping has been demonstrated with better than 500 MHz resolution from 100 GHz to 2 THz. The coherent detection sensitivity is shown to be in good agreement with previous theoretical predictions and yields a signal-to-noise ratio of 90 dB/Hz at 100 GHz and 60 dB/Hz at 1 THz through a path length in air of one foot. The spectrometer frequency resolution and dynamic range are suitable for applications involving analysis of chemical, biological, and explosive materials in solid-phase and gas-phase at atmospheric pressure.

Figure 3:
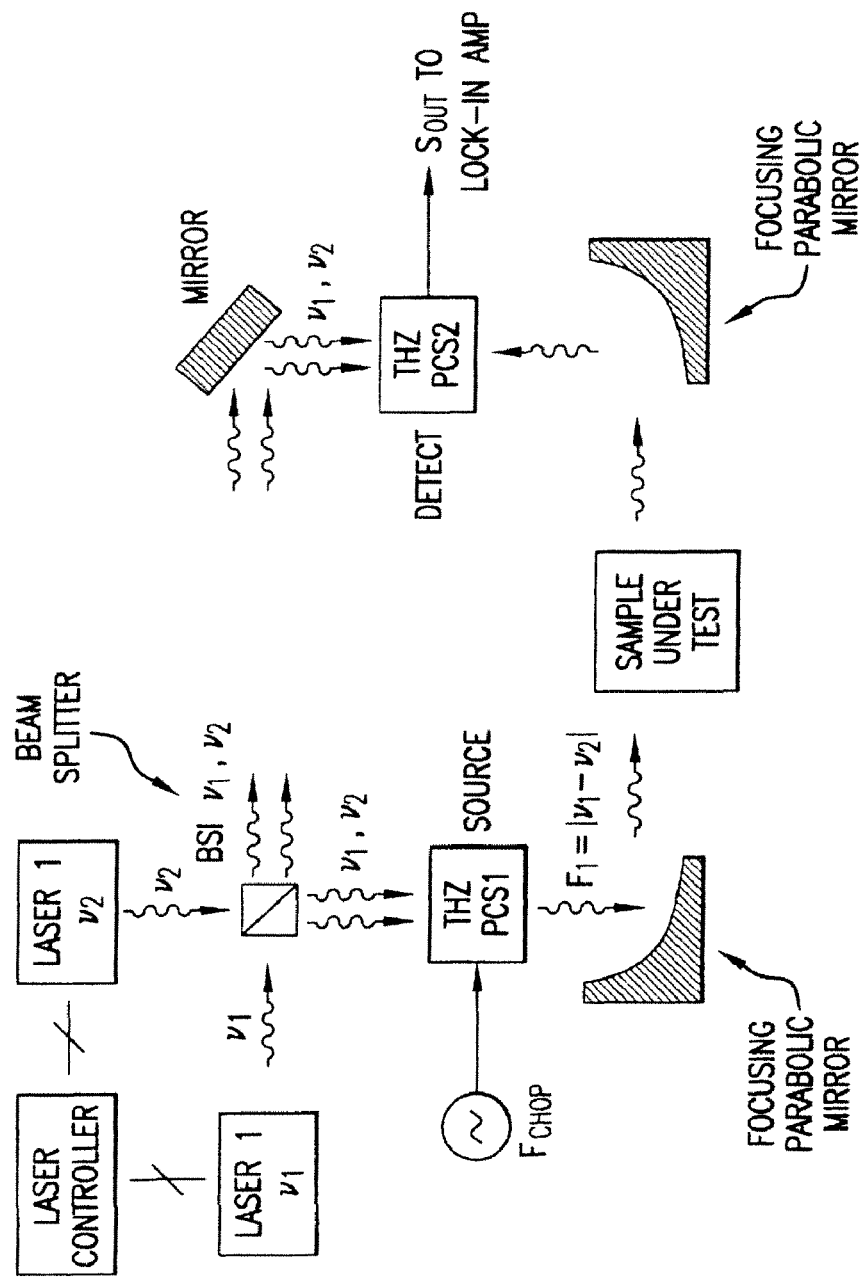
FIG. 3 is a block diagram of a frequency-domain THz spectrometer according to the prior art, for the purposes of illustrating the similarities with a Mach-Zehnder interferometer, as well as how the interferogram arises in data sets collected by a frequency-domain terahertz spectrometer.

Turning our attention now to FIG. 3, there is shown a schematic of a contemporary commercially available system, wherein the source PCS may be electronically chopped at a baseband frequency in the range of DC to several MHz using a differential signal with amplitude varied in a square wave from +Vchop to −Vchop. Chopping is typically used in conjunction with coherent homodyne detection as described above so that a lock-in amplifier tuned to the chopping frequency can be employed to limit the detection noise bandwidth. In previous optical chopping techniques, the optical beam illuminating the PCS is chopped with a segmented vane chopper as known in the art. Since the generated THz voltage is proportional to the incident laser power times the bias voltage applied across the PCS terminals, electronic chopping with a differential signal produces twice the peak THz voltage amplitude from the PCS, which leads to a factor of 4 improvement in generated THz signal power for a given level of optical illumination, compared to optical chopping. This leads to an improvement in signal-to-noise ratio of the present invention, compared to coherent detection with optical chopping.

The optical heterodyne signal, incident on both PCS1 and PCS2, makes this system shown in FIG. 3 a coherent homodyne system in which the THz signal incident on PCS2 is down-converted via multiplication with the generated THz signal due to the optical input to PCS2. A chopping signal is applied to the bias of PCS1 at frequency $F_{chop}$. The detection output signal $S_{out}$ from PCS2 is processed with a lock in amplifier tuned to $F_{chop}$.

As the THz frequency is tuned through a series of frequencies, $S_{out}$ is collected by a computer system at each frequency. In this way, the absorption or reflection spectrum of the sample under test can be collected with high resolution and high signal-to-noise ratio since all of the THz energy is centered in a single tone and the lock-in amplifier limits the noise bandwidth. This, incidentally, is a major advantage of this technique compared to time-domain techniques in which the THz energy is spread over many frequencies.

An undesirable effect of the coherent homodyne set-up due in-part to its inherent structure as an unbalanced interferometer, is the fluctuation of output voltage when tuning the THz frequency. As can be appreciated by those skilled in the art, this is somewhat analogous to an unbalanced optical interferometer subjected to laser frequency drift or bias point drift associated with Mach-Zehnder optical waveguide modulators fabricated in lithium niobate. As is generally known, these devices are prone to bias point drift due—in part—to mobile charges in the optical crystal generated by temperature excursions. In Mach-Zehnder modulators, this effect may be compensated through the use of a feedback circuit that adjusts the relative phase of the two interferometer arms to maintain a desired bias point.

Figure 4:
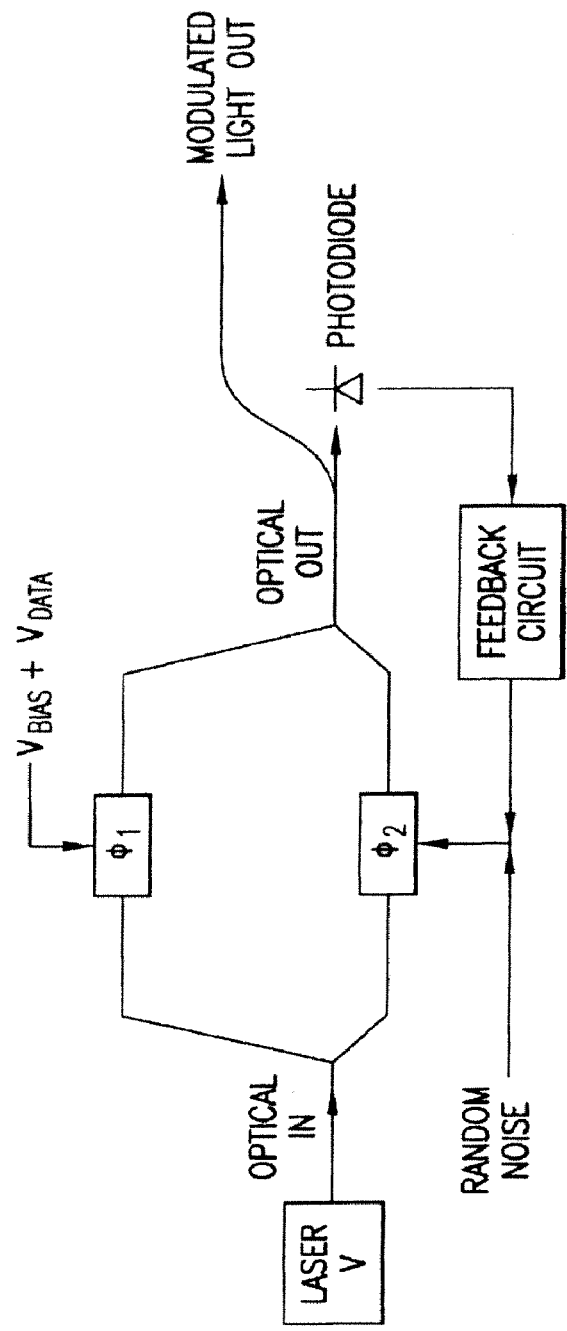
FIG. 4 is a block diagram of a Mach-Zehnder interferometric optical modulator, relevant to the discussion of the interferogram that arises in data sets collected by a frequency-domain terahertz spectrometer.

Such a Mach-Zehnder feedback circuit is shown schematically in FIG. 4 which illustrates a basic Mach-Zehnder modulator with a bias-control feedback circuit, and a purposely-exaggerated path-length imbalance between the two arms. The transfer function for an unbalanced optical interferometer exhibits peaks and nulls as the optical input frequency is varied. A THz spectrometer such as that shown in FIGS. 1 and 2 has a similar topology, and therefore also exhibits a similar response. It would be advantageous to correct for this response, or to measure it precisely to extract useful information from the response, as the laser difference frequency is swept.

Figure 5:
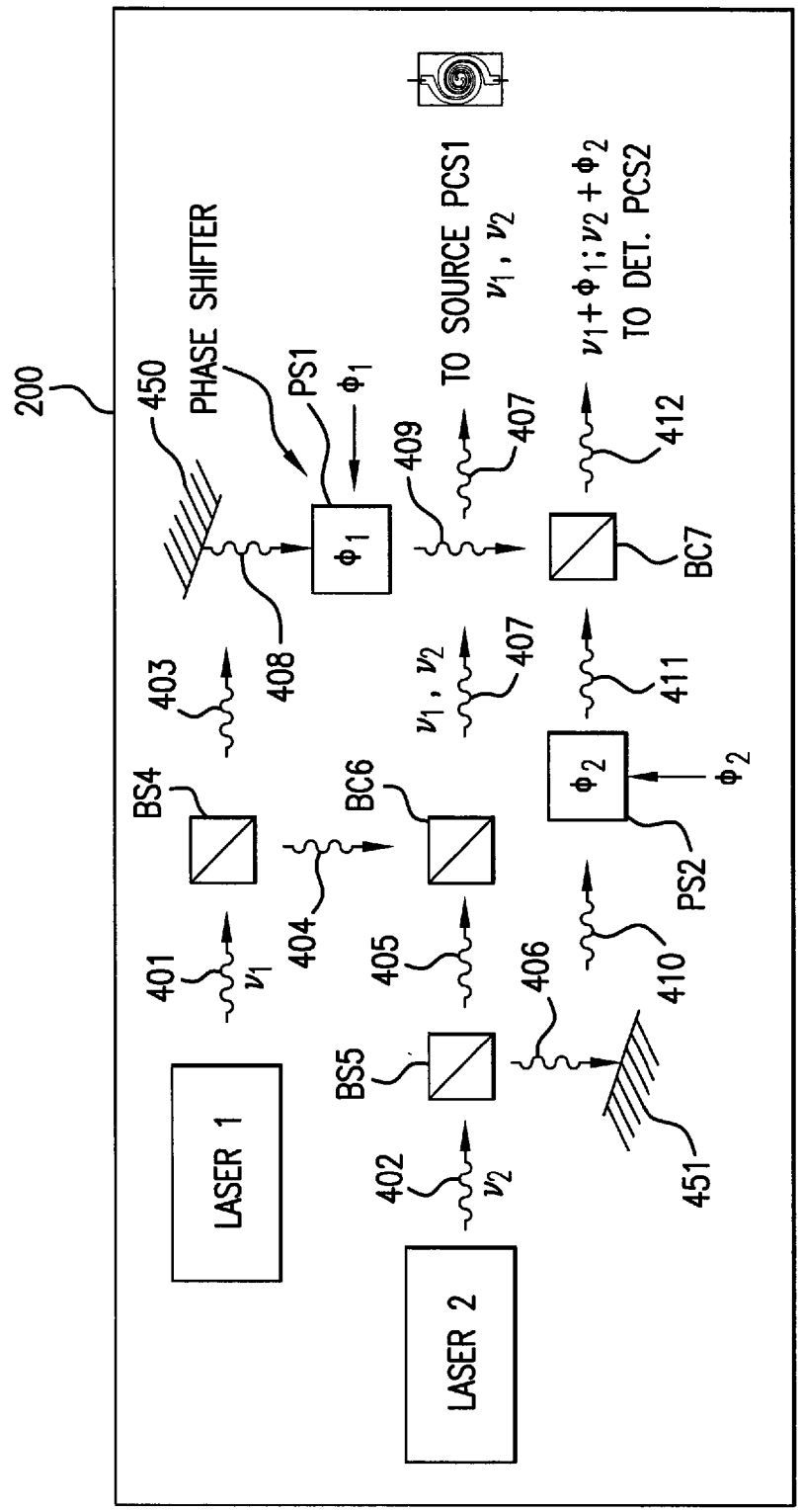
FIG. 5 is a block diagram of a terahertz spectrometer with a phase shifter according to the first embodiment of the present invention.

One approach may be to introduce a phase control element into one arm of the THz interferometer, and apply feedback to the phase control element such that the output voltage at each frequency is maximized. However, to do this, a phase-shift of a full cycle of the lowest THz operating frequency is required. Unfortunately, such a phase shift might be several millimeters of length which is difficult or impossible to achieve by conventional electronic means, such as by introducing a variable phase-shifter into either of the THz or optical paths. Advantageously, and according to an aspect of the present invention, a THz phase shift at the PCS2 detector—relative to the phase of the THz signal generated at the source PCS1—can be achieved by shifting the phase, in a very specific way, of the laser light output subsequently incident on PCS2. FIG. 5 is a schematic of such an arrangement according to an aspect of the present invention.

Turning now to that FIG. 5, there is shown in schematic form a block diagram of the arrangement which employs phase control according to an aspect of the present invention.

With continued reference to FIG. 5, there is shown two lasers, Laser 1 and Laser 2, the outputs of which are shown as 401 and 402 at $v_1$ and $v_2$, respectively. The light output from Laser 1 is 401 directed to a beam splitter BS4 where it is split into two beams, 403, 404. Note that with this exemplary embodiment, the beam splitters employed are substantially 50/50 splitters, although certain variations are within the range of design choice(s).

The split beams 403, 404 output by Laser 1 are preferably directed along separate optical paths. Split beam 403 is directed to a phase shifter PS1 which effects a phase shift of substantially $\Phi_1$ into the split beam 408, thereby resulting in a split beam 409 substantially at frequency $v_1$ and phase shifted by an amount $\Phi_1$. As can be appreciated, geometric or other packaging concerns may make it advantageous to re-direct or focus the split beams through the effect of mirrors 450 or other optical components which may advantageously produce re-directed split beam 408. Of course, such redirection—while shown here as preceding the phase shifter PS1, may in fact be positioned subsequent to the phase shifter as desired.

Similarly the light output from Laser 2 402 is directed to a beam splitter BS5 where it is split into two beams, 405, 406. As noted previously, with this exemplary embodiment, the beam splitters employed are substantially 50/50 splitters, although certain variations are contemplated.

The split beams 405, 406 output by Laser 2 likewise are preferably directed along separate optical paths. Split beam 406 is directed to a phase shifter PS2 which effects a phase shift of substantially $\Phi_2$ into the split beam 410, thereby resulting in a split beam 411 substantially at frequency $v_2$ and phase shifted by an amount $\Phi_2$. As can be appreciated, geometric or other packaging concerns may make it advantageous to re-direct or focus the split beams through the effect of mirrors 451 or other optical components which may advantageously produce re-directed split beam 410. Of course, such redirection—while shown here as preceding the phase shifter PS2, may in fact be positioned subsequent to the phase shifter as desired.

Continuing with the discussion of FIG. 5, the two separate, phase shifted split beams 409 and 411 which originated from Laser 1 and Laser 2 respectively, are combined through the effect of beam combiner BC7 into a combined, phase shifted beam 412. This combined, phase shifted beam 412 is a combination of light having frequency $v_1$, phase shifted by an amount $\Phi_1$, and light having frequency $v_2$, phase shifted by an amount $\Phi_2$ and is directed to the detector PCS2 (not specifically shown in this FIG. 5.).

Shown further in FIG. 5, the other split beams from Laser 1 and Laser 2 namely beam 404 and 405 respectively, are combined through the effect of beam combiner BC6. More particularly individual split beams 404 and 405 are combined through the effect of combiner BC6 into combined beam 407 at frequencies $v_1$ and $v_2$. This combined beam 407 is then directed to source PCS1 to effect the generation of THz radiation. As can be readily appreciated by those skilled in the art, this arrangement permits precise phase control of the PCS2 optical signal with respect to the PCS1 optical signal. Consequently, signal processing techniques may be employed to enhance or otherwise effect the output signal at one or more of the sampling frequencies employed to, for example, eliminate interference fringes described previously, or to extract the phase spectrum of a sample under test from the interferogram.

Figure 6:
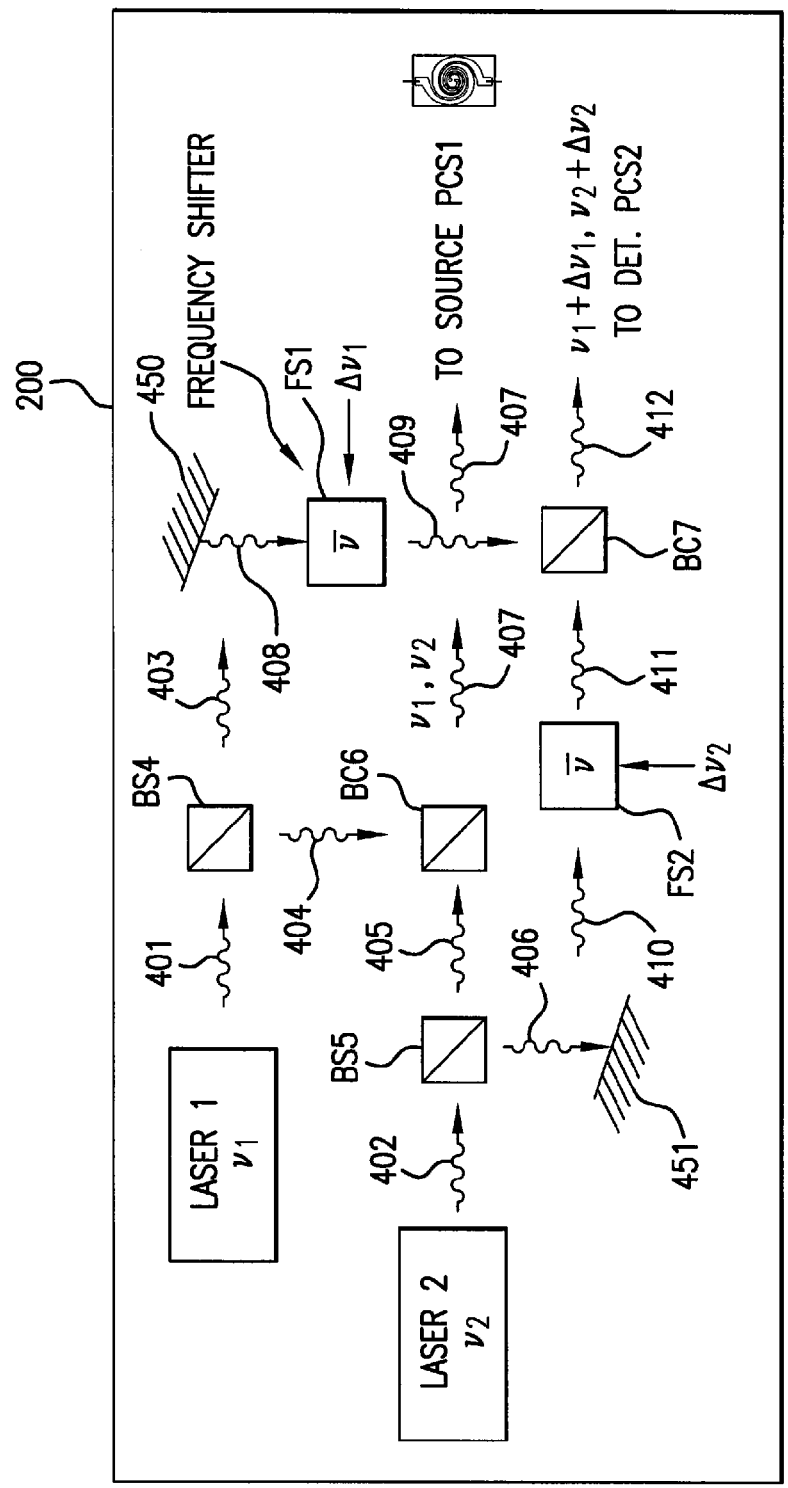
FIG. 6 is a block diagram of a terahertz spectrometer with a frequency shifter according to a second embodiment of the present invention.

According to another aspect of the present invention, the phase shifters may be replaced by a frequency shifter element. Such an embodiment is illustrated in FIG. 6. Advantageously, such configuration enables a coherent heterodyne detection scheme, instead of homodyne detection.

Turning now to that FIG. 6, there is shown in schematic form a configuration according to an aspect of the present invention employing a frequency-shifted, heterodyne detection scheme. Shown in that FIG. 6, are two lasers, Laser 1 and Laser 2, the outputs of which are shown as 401 and 402 at $v_1$ and $v_2$, respectively. The light output from Laser 1 is 401 directed to a beam splitter BS4 where it is split into two beams, 403, 404.

The split beams 403, 404 output by Laser 1 are directed along separate optical paths. Split beam 403 is directed to a frequency shifter FS1 which effects a frequency shift of substantially $\Delta v_1$ into the split beam 408, thereby resulting in a split beam 409 originally at frequency $v_1$ and now frequency shifted by an amount $\Delta v_1$. As can be appreciated and previously noted, geometric or other packaging concerns may make it advantageous to re-direct or focus the split beams through the effect of mirrors 450 or other optical components which may advantageously produce re-directed split beam 408. Of course, such redirection—while shown here as preceding the frequency shifter FS1, may in fact be positioned subsequent to the frequency shifter as desired.

Similarly the light output from Laser 2 402 is directed to a beam splitter BS5 where it is split into two beams, 405, 406. The split beams 405, 406 output by Laser 2 likewise are preferably directed along separate optical paths. Split beam 406 is directed to a frequency shifter FS2 which effects a frequency shift of substantially $\Delta v_2$ into the split beam 410, thereby resulting in a split beam 411 substantially at frequency $v_2+\Delta v_2$. In other words, the original split beam 410 at frequency $v_2+\Delta v_2$ is frequency shifted by an amount $\Delta v_2$.

The two separate, frequency shifted split beams 409 and 411 which originated from Laser 1 and Laser 2 respectively, are combined through the effect of beam combiner BC7 into a combined, frequency shifted beam 412. This combined, frequency shifted beam 412 is a combination of light having frequency $v_1+\Delta v_1$, and light having frequency $v_2+\Delta v_2$, and is directed to the detector PCS2 (not specifically shown in this FIG. 6.).

The other split beams from Laser 1 and Laser 2 namely beam 404 and 405 respectively, are combined through the effect of beam combiner BC6. More particularly individual split beams 404 and 405 are combined through the effect of combiner BC6 into combined beam 407 at frequencies $v_1$ and $v_2$. This combined beam 407 is then directed to source PCS1 to effect the generation of THz beam(s) for subsequent irradiation of a target sample.

In summary, certain aspects of the present invention may provide a compact frequency-domain terahertz coherent spectrometer with continuous tuning from 100 GHz to over 2 THz. Such construction may employ highly compact photonic integration techniques, electronic differential chopping, and room-temperature coherent THz detection. Advantageously, such devices may offer rapid identification of chemical, biological and explosive materials in both the solid-phase and the gas-phase at standard atmospheric pressure. The highly integrated photonic assembly employing semiconductor diode lasers employs no moving parts and is inherently rugged and well-suited to field-deployable applications. Also, the coherent (homodyne) detection technique provides excellent SNR in agreement with theory, with much faster data acquisition times and no cryogenic cooling as required by the liquid He bolometers in more common (incoherent) THz photomixing spectrometers. Also, a frequency-shifter embodiment similar to the arrangement of FIG. 6, but in which the frequency-shifted optical beams are incident on the source PCS, provides a means to effect extremely high-resolution spectroscopy. This is achieved via the ability to adjust the frequency of the source optical heterodyne signal with finer resolution than is typically possible using thermal control of the lasers alone. Typical thermal tuning resolution and accuracy may only be 250 MHz, whereas the electronic tuning can be at the Hz level.

Of course, various modifications and improvements of the present invention may also be apparent to those of ordinary skill in the art. Thus, the particular combination of parts described and illustrated herein is intended to represent only certain embodiments of the present invention, and is not intended to serve as limitations of alternate devices within the spirit and scope of the invention.

It will be understood that each of the elements described above, or two or more together, also may find a useful application in other types of constructions differing from the types described above. In particular, certain configurations presented according to particular aspects of the present invention have been shown and described as discrete elements, i.e., lasers, splitters, combiners, mirrors, lenses, shifters, etc. Those skilled in the art will readily appreciate that many or all of these individual, discrete components may be fabricated and/or packaged into integrated elements. By way of particular example, the use of integrated waveguides and associated structures is envisioned for the described structures and arrangements. Alternatively, the discrete elements, i.e., lasers, splitters, combiners, mirrors, lenses, shifters, etc. may also be individually-packaged in modules with optical fiber interconnects to achieve the same topology and functionality.

While the invention has been illustrated and described as embodied in terahertz transceiver or spectrometer system, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected" or "operably coupled" to each other to achieve the desired functionality.

While particular embodiments of the present invention have been shown and described, it will be understood by those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," "comprise" and variations thereof, such as, "comprises" and "comprising" are to be construed in an open, inclusive sense, that is as "including, but not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

What is claimed:

1. An apparatus for analyzing, identifying, or imaging a target, said apparatus comprising:
   first and second lasers having tunable frequencies, said first laser to produce a first output beam and said second laser to produce a second output beam, said first output beam and said second output beam having different frequencies, wherein a first portion of said first output beam and a first portion of said second output beam are to produce a first composite output beam;
   a source of CW signals in the range of frequencies from 100 GHz to over 2 THz including a first photoconductive switch activated by said first composite output beam;
   a radiative element for causing said CW signals to be substantially simultaneously focused on or through said target;
   a first phase shifting element positioned to receive a second portion of said first output beam to controllably adjust the phase of said second portion of said first output beam with respect to a second portion of said second output beam;
   an optical element to produce a second composite output beam from said second portion of said first output beam and said second portion of said second output beam, wherein said second composite output beam has an adjustable phase difference with respect to said first composite output beam; and
   a detector for,
      acquiring spectral information from said target,
      receiving said second composite output beam, and
      generating, based on said spectral information and said second composite output beam, an electrical signal representative of a characteristic of said target.

2. An apparatus as defined in claim 1, wherein said detector includes a second photoconductive switch activated by said second composite output beam.

3. An apparatus as defined in claim 1, said apparatus further comprising a processor coupled to said detector for analyzing said electrical signal and determining said characteristic of said target based upon the absorption characteristics of said target in the 100 GHz to over 2 THz frequency band.

4. An apparatus as defined in claim 1, wherein said first and second lasers are DFB or DBR lasers.

5. An apparatus as defined in claim 1, wherein said first photoconductive switch is a low temperature grown ErAs; GaAs photoconductive switch.

6. An apparatus as defined in claim 1, said apparatus further comprising a second phase shifting element positioned to receive said second portion of said second output beam to controllably adjust the phase of said second portion of said second output beam.

7. A method for analyzing, identifying, or imaging a target, said method comprising:
  providing first and second lasers having tunable frequencies, said first laser to produce a first output beam and said second laser to produce a second output beam, said first output beam and said second output beam having different frequencies, wherein a first portion of said first output beam and a first portion of said second output beam are to produce a first composite output beam;
  generating CW signals in the range of frequencies from 100 GHz to over 2 THz using said first composite output beam;
  causing said CW signals to be substantially simultaneously focused on or through said target;
  positioning a first phase shifting element to receive a second portion of said first output beam to controllably adjust the phase of said second portion of said first output beam with respect to a second portion of said second output beam;
  providing an optical element to produce a second composite output beam from said second portion of said first output beam and said second portion of said second output beam, wherein said second composite output beam has an adjustable phase difference with respect to said first composite output beam;
  acquiring a spectral information signal from said target; and
  generating an electrical signal representative of a characteristic of said target based on said spectral information signal and said second composite output beam.

8. A method as defined in claim 7, said method further comprising positioning a second phase shifting element to receive said second portion of said second output beam to controllably adjust the phase of said second portion of said second output beam.

9. A method as defined in claim 7, wherein generating said CW signals includes activating a first photoconductive switch using said first composite output beam.

10. A method as defined in claim 9, wherein generating said electrical signal includes activating a second photoconductive switch using said second composite output beam.

11. A method as defined in claim 7, said method further comprising determining said characteristic of said target based upon the absorption characteristics of said target in the 100 GHz to over 2 THz frequency band.

12. A method for analyzing, identifying, or imaging a target, said method comprising:
  providing first and second lasers having tunable frequencies, said first laser to produce a first output beam and said second laser to produce a second output beam, said first output beam and said second output beam having different frequencies;
  producing a first composite output beam from a first portion of said first output beam and a first portion of said second output beam;
  producing a second composite output beam from a second portion of said first output beam and a second portion of said second output beam, wherein said second composite output beam has an adjustable frequency difference with respect to said first composite output beam;
  generating CW signals in the range of frequencies from 100 GHz to over 2 THz using said first composite output beam;
  causing said CW signals to be substantially simultaneously focused on or through said target;
  acquiring a spectral information signal from said target; and
  generating an electrical signal representative of a characteristic of said target based on said spectral information signal and said second composite output beam.

13. A method as defined in claim 12, wherein producing said second composite output beam from said second portion of said first output beam and said second portion of said second output beam includes controllably adjusting the frequency of said second portion of said first output beam such that said second composite output beam has said adjustable frequency difference with respect to said first composite output beam.

14. A method as defined in claim 12, wherein producing said first composite output beam from said first portion of said first output beam and said first portion of said second output beam includes controllably adjusting the frequency of said first portion of said first output beam such that said second composite output beam has said adjustable frequency difference with respect to said first composite output beam.

15. A method as defined in claim 12, wherein generating said CW signals includes activating a first photoconductive switch using said first composite output beam.

16. A method as defined in claim 15, wherein generating said electrical signal includes activating a second photoconductive switch using said second composite output beam.

17. A method as defined in claim 12, said method further comprising determining said characteristic of said target based upon the absorption characteristics of said target in the 100 GHz to over 2 THz frequency band.

* * * * *